(12) United States Patent
White

(10) Patent No.: US 9,506,782 B2
(45) Date of Patent: Nov. 29, 2016

(54) APPARATUS AND METHOD FOR APPLYING A LOAD TO A MATERIAL

(71) Applicant: Bose Corporation, Framingham, MA (US)

(72) Inventor: Andrew D. White, Minneapolis, MN (US)

(73) Assignee: Bose Corporation, Framingham, MA (US)

( * ) Notice: Subject to any disclaimer, the term of this patent is extended or adjusted under 35 U.S.C. 154(b) by 817 days.

(21) Appl. No.: 13/869,595

(22) Filed: Apr. 24, 2013

(65) Prior Publication Data

US 2014/0324390 A1    Oct. 30, 2014

(51) Int. Cl.
G01D 18/00    (2006.01)
G05B 13/04    (2006.01)
G05B 13/02    (2006.01)

(52) U.S. Cl.
CPC ........... *G01D 18/00* (2013.01); *G05B 13/0205* (2013.01); *G05B 13/04* (2013.01)

(58) Field of Classification Search
USPC .................................................. 702/189, 191
See application file for complete search history.

(56) References Cited

U.S. PATENT DOCUMENTS

| 4,766,967 | A | * | 8/1988 | Slicker et al. | 180/54.1 |
| 5,483,438 | A | * | 1/1996 | Nishimura | 700/29 |
| 7,031,886 | B1 | * | 4/2006 | Hargreaves | 702/191 |
| 7,142,930 | B2 | * | 11/2006 | Shimada et al. | 700/29 |
| 7,319,570 | B2 | * | 1/2008 | Jia et al. | 360/77.02 |
| 8,027,112 | B2 | * | 9/2011 | Jia | 360/39 |
| 2010/0280787 | A1 | | 11/2010 | White et al. | |
| 2011/0203388 | A1 | * | 8/2011 | Kitami et al. | 73/861.356 |
| 2012/0059601 | A1 | * | 3/2012 | Kitami et al. | 702/45 |

FOREIGN PATENT DOCUMENTS

EP    507320 A2    10/1992

OTHER PUBLICATIONS

Wensheng Hua, Dan B. Debra, Corwin T. Hardham, Brian T. Lantz: "Polyphase FIR Complementary Filters for Control Systems", Proceedings of 2004 Spring Topical Meeting on Control of Precision Systems, Apr. 20, 2004 (Apr. 20, 2004), XP002728239, ISBN: 1-887706-35-6, p. 1, col. 1, line 1-line 8.

Steve Soderling et al: "Servo Controller Compensation Methods—Selection of the Correct Technique for Test Applications", Internet Citation, Jan. 1, 1999 (Jan. 1, 1999), pp. 1-13, XP0026000811, Retrieved from the Internet: URL:http://www.cannon-leser.net/master/Christoph/SAEI999-01-3000.pdf [retrieved on Sep. 13, 2010].

(Continued)

*Primary Examiner* — Huan Tran
(74) *Attorney, Agent, or Firm* — Bose Corporation

(57) ABSTRACT

A method of controlling a system using a hybrid feedback signal includes providing an input signal with a predetermined waveform to the system and measuring an output of the system with a sensor. An output signal of the sensor is used in a first frequency band as a first portion of a feedback signal. A simulated signal is created in a second frequency band that has one or more of substantially reduced (i) resonances, (ii) phase delay and (iii) noise when compared to the output signal of the sensor in the second frequency band. The simulated signal is used in the second frequency band as a second portion of the feedback signal.

25 Claims, 4 Drawing Sheets

(56) References Cited

OTHER PUBLICATIONS

Plummer A R: "Control techniques for structural testing: a review", Proceedings of the Institution of Mechanical Engineers, Journal of Engineering in Medicine. Part H, Mechanical Engineering Publications Ltd, London, GB, vol. 221, No. 2, Jan. 1, 2007 (Jan. 1, 2007), pp. 139-169, XP009138580, ISSN: 0954-4119, DOI: 10.1243/09596518JSCE295.

International Search Report and Written Opinion dated Aug. 20, 2014 for International application No. PCT/US2014/034667.

* cited by examiner

APPARATUS AND METHOD FOR APPLYING A LOAD TO A MATERIAL

BACKGROUND

This disclosure relates to systems which can apply a load (e.g. a cyclical load) to a material in order to, for example, determine various characteristics of the material. These types of systems are sold by The Electro Force® Systems Group of Bose Corporation. An example of this type of system is the ElectraForce® 3200 Test Instrument. A linear electromagnetic motor is used to apply the load to the material. A sensor (e.g. a load cell) measures an output of the system while the material is under the load and provides a feedback signal which is used in controlling operation of the motor. Relatively high-frequency resonances and phase delay introduced into the sensor by the system and/or the material being tested can cause the feedback signal to negatively impact the operation of the motor.

SUMMARY

All examples and features mentioned below can be combined in any technically possible way.

In one aspect, a method of controlling a system using a hybrid feedback signal includes providing an input signal with a predetermined waveform to the system and measuring an output of the system with a sensor. An output signal of the sensor is used in a first frequency band as a first portion of a feedback signal. A simulated signal is created in a second frequency band that has one or more of substantially reduced (i) resonances, (ii) phase delay and (iii) noise when compared to the output signal of the sensor in the second frequency band. The simulated signal is used in the second frequency band as a second portion of the feedback signal.

Embodiments may include one of the following features, or any combination thereof. The feedback signal is utilized to alter the input signal. The first frequency band is lower than the second frequency band. A top of the first frequency band is substantially adjacent to a bottom of the second frequency band. The sensor can measure at least one of load, displacement, strain, pressure, torque, stress, and rotation. The method further includes (a) differentially combining the input signal with the feedback signal to obtain an initial control signal, (b) obtaining a first or higher order derivative of the feedback signal, (c) differentially combining the initial control signal with the derivative of the feedback signal to obtain a final control signal, and (d) applying the final control signal to an actuator which causes the actuator to create a load which can be applied to a material.

In another aspect, a method of controlling a system for applying a load to a material includes providing a reference signal having a predetermined waveform and differentially combining the reference signal with a feedback signal to obtain an initial control signal. A first or higher order derivative of the feedback signal is obtained. The initial control signal is differentially combines with the derivative of the feedback signal to obtain a final control signal. The final control signal is applied to an actuator which causes the actuator to create the load which can be applied to a material. A sensor is used to measure an output of the system while the load is being applied to the material. An output signal of the sensor is passed through a low-pass filter to create a low-pass signal.

Embodiments may include one of the above and/or below features, or any combination thereof. The final control signal is processed to obtain a simulated signal that has one or more of substantially reduced resonances, substantially reduced phase delay and substantially reduced noise compared to the output signal of the sensor. The simulated signal is passed through a high-pass filter to obtain a high-pass signal. The low-pass signal and the high-pass signal are combined to create the feedback signal. The low pass filter and the high-pass filter sum to substantially one.

In yet another aspect, an apparatus for applying a load to a material includes a signal generator that can create a reference signal having a predetermined waveform. A first signal combiner can differentially combine the reference signal with a feedback signal to obtain an initial control signal. A signal manipulator can obtain a first or higher order derivative of the feedback signal. A second signal combiner can differentially combine the initial control signal with the derivative of the feedback signal to obtain a final control signal. The final control signal can be applied to an actuator to cause the actuator to create the load which can be applied to the material. The final control signal is processed to obtain a simulated signal that has one or more of substantially reduced resonances and substantially reduced phase delay compared to the an output signal of a sensor used to measure an output of the apparatus while the load is applied to the material.

Embodiments may include one of the above and/or below features, or any combination thereof. The simulated signal is passed through a high-pass filter to obtain a high-pass signal. The output signal of the sensor is passed through a low-pass filter to create a low-pass signal. The low-pass signal and the high-pass signal are combined to create the feedback signal. The low-pass filter and the high-pass filter sum to substantially one.

In yet another aspect, a method of controlling a system for applying a load to a material includes applying a final control signal to an actuator which causes the actuator to create the load which can be applied to the material. A sensor is caused to measures an output of the system while the load is being applied to the material. An output signal is read from the sensor. The final control signal is processed to obtain a simulated signal that has one or more of substantially reduced resonances and substantially reduced phase delay compared to the output signal. The simulated signal is passed through a filter mechanism to obtain a high-pass signal.

Embodiments may include one of the above and/or below features, or any combination thereof. An output signal of the sensor is passed through the filter mechanism to create a low-pass signal. The filter mechanism includes a low-pass filter and a high-pass filter which sum to one. A reference signal having a predetermined waveform is input to the system. The reference signal is differentially combined with the feedback signal to obtain an initial control signal. The sensor measures a characteristic of the material.

DETAILED DESCRIPTION

The description below discusses a system for applying a load to a material with a linear electromagnetic motor. A sensor (e.g. a load cell) measures an output of the system while the load is applied to the material and provides a feedback signal which is used in controlling operation of the motor. Resonances and phase delay introduced into the sensor by the system and/or the material being tested tend to be present in a frequency band that is relatively higher than the frequency band in which the load is intended to be applied to the material. The output of the sensor is passed through a filter mechanism to obtain a low pass filtered signal. The final signal that controls operation of the motor is processed to compute a simulated signal that has substantially reduced resonances and/or phase delay compared to the final control signal in the relatively higher-frequency band. The simulated signal is passed through the filter mechanism to obtain a high pass filtered signal and then combined with the low-pass filtered signal from the sensor to provide an updated feedback signal. As a result, the system is converted into a 2nd (or higher) order system with no phase delay.

Figure 1:
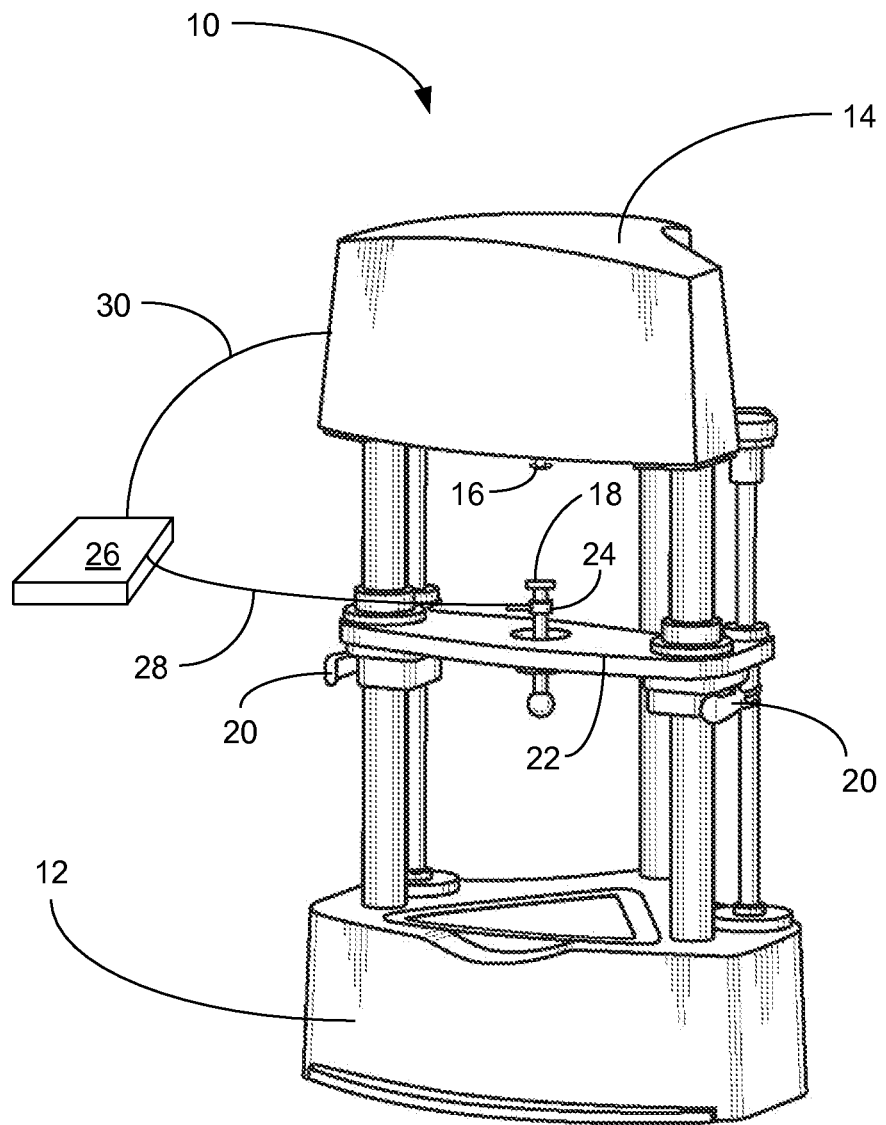
FIG. 1 is perspective view of a system for applying a load to a material.

Referring to FIG. 1, a system 10 for applying a load to a material sample (not shown) includes a lower housing 12 and an upper housing 14. An actuator in the form of a linear electro-magnetic motor (not shown) is contained within the upper housing 14. The material is placed between an upper sample grip 16 and a lower sample grip 18. The distance between the grips is adjusted in order to secure the material between the grips. This is done by opening a pair of clamps 20, raising or lowering a stage 22 to which the lower grip is secured, and then closing the clamps 20. Depending on the material type, different types of grips can be used to secure the material. The motor can move the upper grip 16 (e.g. up and down) to apply a load to the material secured between the grips. The lower grip 18 is secured in a stationary position when the load is being applied to the material. Various types of loads such as compression, tension, torque, bending, etc. can be applied to the material depending on the arrangement of the system 10.

A sensor 24 (e.g. a load cell) measures an output of the system 10 (which can include a characteristic of the material) while the load is being applied to the material via the sample grips 16 and 18. Various types of sensors can be used to measure a number of different outputs of the system such as load, displacement, strain, stress, velocity, acceleration, pressure, torque, rotation etc. A processor 26 is part of and controls the operation of the system 10. The processor is connected to the sensor 24 and the system 10 (to control the motor) by respective data buses 28 and 30. Electrical power to the system 10 is provided by AC mains. The power to some or all of the system 10 may be conditioned by a power supply and a transformer.

Figure 2:
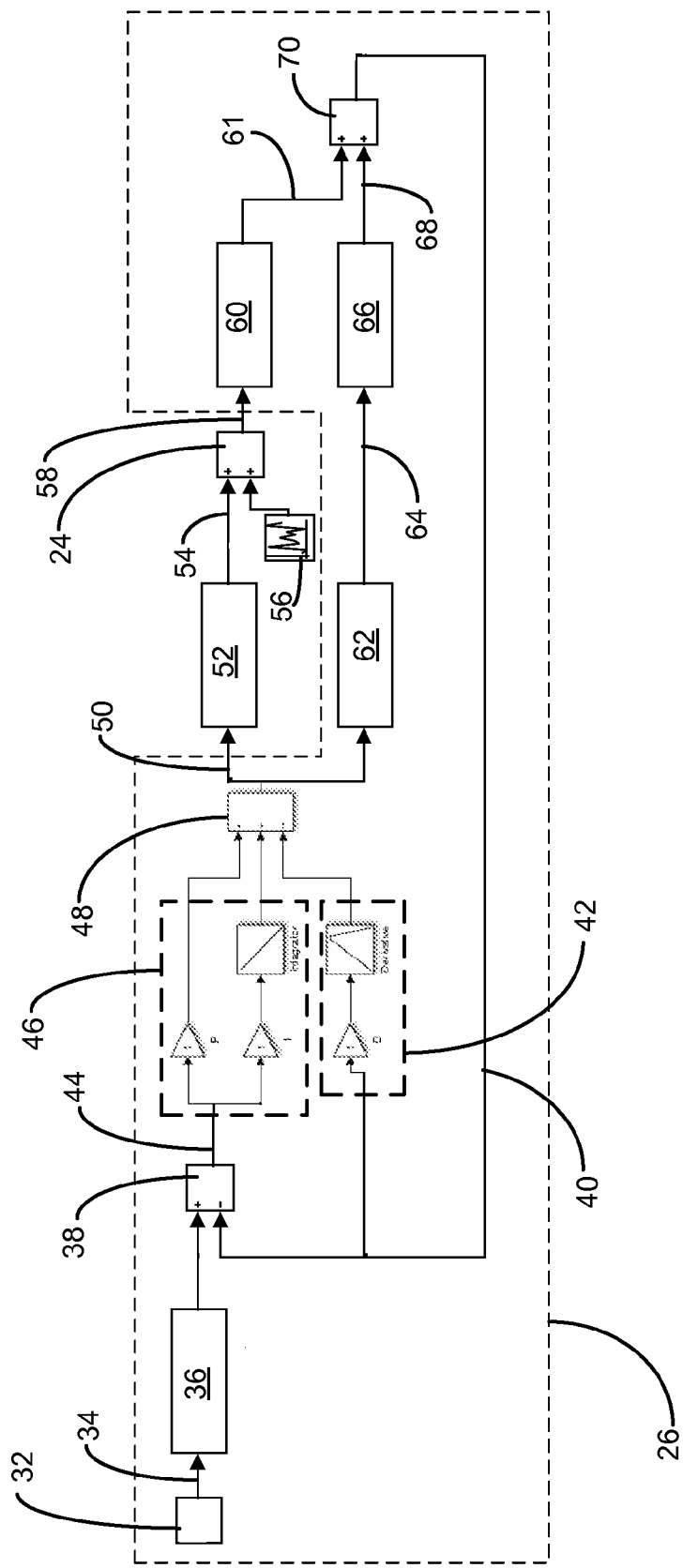
FIG. 2 is a block diagram of a signal processing arrangement used in the system of FIG. 1.

Turning to FIG. 2, the processor 26 includes a signal generator 32 that can provide a reference (input) signal 34 having a predetermined waveform (e.g., a sine wave having a known frequency and amplitude) to the system 10. The reference signal is then passed through a low-pass filter 36 with a cutoff of, for example, 100 Hz. The reference signal outputted from the low-pass filter 36 is passed to a signal combiner 38 where it is differentially combined with a feedback signal 40. The feedback signal 40 is also passed to a derivative block 42 where the signal is manipulated to obtain a first or higher order derivative of the feedback signal. The output of the combiner 38 in the form of an initial control signal 44 is processed in a proportional-integral (PI) block 46. The initial control signals out of the PI block 46 are differentially combined with the derivative of the feedback signal out of the derivative block 42 in a signal combiner 48.

The output of the combiner 48 in the form of a final control signal 50 is applied to an actuator 52 (mentioned above with respect to FIG. 1). A digital-to-analog convertor (not shown) converts the final control signal 50 from a digital form to an analog form prior to this signal being applied to the actuator 52. As described above, the actuator 52 creates a load 54 which is applied to a material sample via a pair of sample grips 16, 18. A characteristic or output (e.g. load) of the system 10 is measured by the sensor 24 while the sample is under the load. The signal output by the sensor 24 also includes resonances 56 (which may have associated phase delays) from the system 10 and/or the material sample as the sensor is vibrated by these resonances. An output signal 58 of the sensor 24 is converted from an analog form to a digital form by an analog-to-digital convertor (not shown) and then is passed to a low-pass filter 60 of a filter mechanism to create a low-pass signal 61 in a first frequency band.

The final control signal 50 is also passed to a simulation block 62 where the signal is processed to obtain a simulated signal 64 that has one or more of substantially reduced (a) resonances, (b) noise and (c) phase delay compared to the output signal 58. The simulated signal 64 is passed through a high-pass filter 66 of the filter mechanism to create a high-pass signal 68 in a second frequency band which is higher than the first frequency band mentioned at the end of the previous paragraph. Preferably, a top of the first frequency band is substantially adjacent to a bottom of the second frequency band. In one example the low- and high-pass filters 60 and 66 sum substantially to one with a cross-over of, for example, 100 Hz. It is not necessary that the low and high pass filters 60 and 66 sum to one. The low-pass signal 61 and high-pass signal 68 are additively combined in a signal combiner 70 which outputs the feedback signal 40. The feedback signal 40 is effectively a hybrid feedback signal which is used in controlling the system 10. As a result, the feedback signal also has one or more of substantially reduced (a) resonances, (b) noise and (c) phase delay compared to the output signal 58. The feedback signal 40 is utilized in altering the input signal 34 as required.

Figure 3:
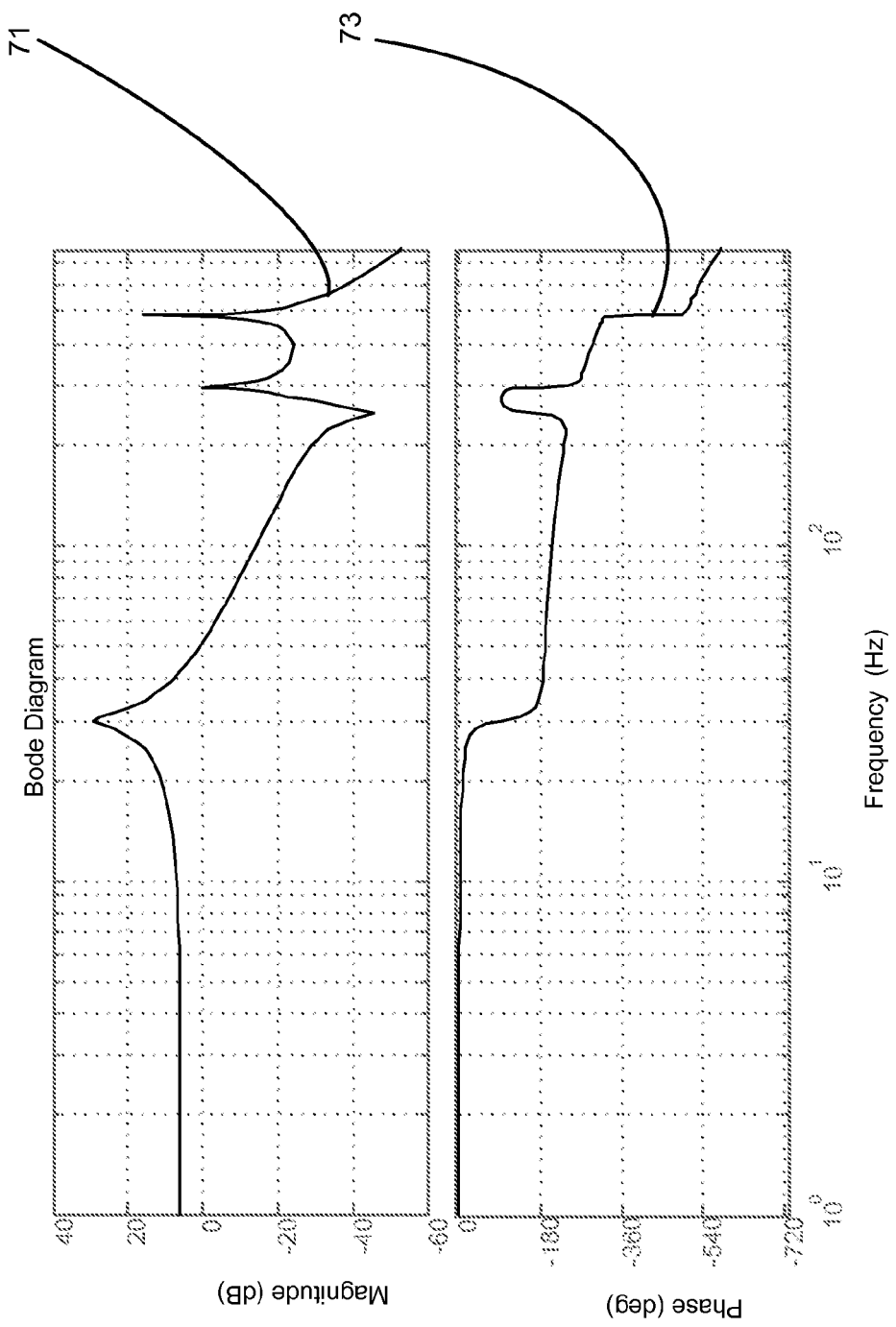
FIG. 3 is a logarithmic plot of phase and magnitude relative to frequency for an output of a load cell of the system of FIG. 1.

With reference to FIG. 3, the magnitude 71 and phase 73 of the output signal 58 of the sensor 24 are logarithmically plotted versus frequency. A 30 Hz signal has been applied by the actuator 52 to the material sample. Of note is the low damping of the resonances and the phase delay due to the electronic system. Resonances with associated phase delays from the system 10 and/or the material sample are present in the signal above 200 Hz. The relatively close spacing in frequency of the resonance peaks can raise issues with controlling the system 10.

Figure 4:
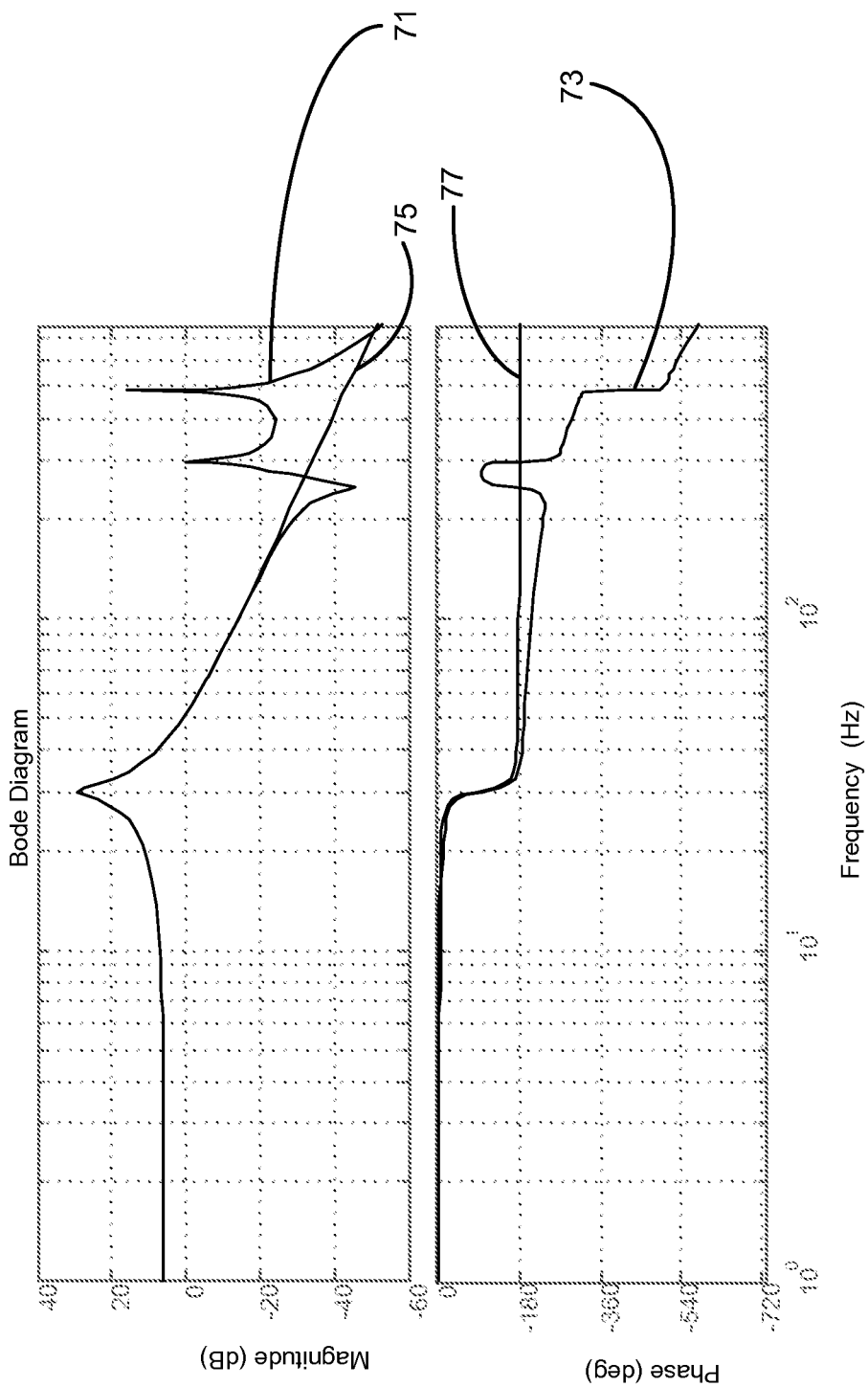
FIG. 4 is similar to FIG. 3 but also includes a plot of a feedback signal.

FIG. 4 is similar to FIG. 3 but includes a plot of the magnitude 75 and phase 77 of the feedback signal 40 as well. The magnitudes 71 and 75 of the output signal 58 and the feedback signal 40 are substantially the same up to about 150 Hz. The phases 73 and 77 of the output signal 58 and the feedback signal 40 are substantially the same phase up to about 40 Hz. Notice that the resonance peaks above 200 Hz in the magnitude 71 of the output signal 58 have been damped out in the magnitude 75 of the feedback signal 40. In addition, the substantial phase delays above 200 Hz in the phase 73 of the output signal 58 have been substantially eliminated in the phase 77 of the feedback signal 40.

The system described above has minimal or no stability issues with system convergence as the error between the outputs of the sensor 24 and simulation block 62 is not being actively compensated. In addition, model accuracy in the simulation block 62 is significantly less important than would be required in a state space observer model. In the state space observer model, inaccuracies can lead to long convergence times, lower performance, and/or stability issues. For the system 10 described above, the error estimating the primary resonance frequency and gain in the simulation block 62 can be large (>50% error) with minimal penalties. Further advantages include (a) higher system bandwidth, (b) greater disturbance rejection, (c) improved system stability (higher margins), (d) reduction in controller generated noise, and (e) no or minimal high frequency penalty for sampled data systems (elimination of time delay).

The system described above discusses a displacement type of load (compression and/or tension). Other types of loads (e.g. torque, bending, strain, pressure) can be applied to the sample by changing the relative movement between the grips and the sample. In addition, other types of sensors (e.g. a hoop strain gauge, an accelerometer, etc.) besides a load cell can be used to measure a characteristic or output of the system 10 when the sample material is being loaded.

A number of implementations have been described. Nevertheless, it will be understood that additional modifications may be made without departing from the scope of the inventive concepts described herein, and, accordingly, other embodiments are within the scope of the following claims.

What is claimed is:

1. A method of controlling a system using a hybrid feedback signal, comprising:
   providing an input signal with a predetermined waveform to the system;
   measuring an output of the system with a sensor;
   using an output signal of the sensor in a first frequency band as a first portion of a feedback signal;
   creating a simulated signal in a second frequency band that has one or more of substantially reduced (i) resonances, and (ii) phase delay when compared to the output signal of the sensor in the second frequency band; and
   using the simulated signal in the second frequency band as a second portion of the feedback signal.

2. The method of claim 1, further including utilizing the feedback signal to alter the input signal.

3. The method of claim 1, wherein the first frequency band is lower than the second frequency band.

4. The method of claim 3, where a top of the first frequency band is substantially adjacent to a bottom of the second frequency band.

5. The method of claim 1, wherein the sensor can measure at least one of load, displacement, strain, pressure, torque, stress, and rotation.

6. The method of claim 1, further including (a) differentially combining the input signal with the feedback signal to obtain an initial control signal, (b) obtaining a first or higher order derivative of the feedback signal, (c) differentially combining the initial control signal with the derivative of the feedback signal to obtain a final control signal, and (d) applying the final control signal to an actuator which causes the actuator to create a load which can be applied to a material.

7. A method of controlling a system for applying a load to a material, comprising:
   providing a reference signal having a predetermined waveform;
   passing the reference signal through a low pass filter;
   differentially combining the low pass filtered reference signal with a feedback signal to obtain an initial control signal;
   obtaining a first or higher order derivative of the feedback signal;
   differentially combining the initial control signal with the derivative of the feedback signal to obtain a final control signal;
   applying the final control signal to an actuator which causes the actuator to create the load which can be applied to a material;
   using a sensor to measure an output of the system while the load is being applied to the material; and
   passing an output signal of the sensor through a low-pass filter to create a low-pass signal.

8. The method of claim 7, further including processing the final control signal to obtain a simulated signal that has one or more of substantially reduced resonances and substantially reduced phase delay compared to the output signal of the sensor.

9. The method of claim 8, further including passing the simulated signal through a high-pass filter to obtain a high-pass signal.

10. The method of claim 9, further including combining the low-pass signal and the high-pass signal to create the feedback signal.

11. The method of claim 9, wherein the low pass filter and the high-pass filter sum to substantially one.

12. An apparatus for applying a load to a material, comprising:
   a signal generator that can create a reference signal having a predetermined waveform;
   a first signal combiner that can differentially combine the reference signal with a feedback signal to obtain an initial control signal;
   a signal manipulator that can obtain a first or higher order derivative of the feedback signal;
   a second signal combiner that can differentially combine the initial control signal with the derivative of the feedback signal to obtain a final control signal; and
   an actuator to which the final control signal can be applied to cause the actuator to create the load which can be applied to the material, wherein the final control signal is processed to obtain a simulated signal that has one or more of substantially reduced resonances and substantially reduced phase delay compared to an output signal of a sensor used to measure an output of the apparatus while the load is applied to the material.

13. The apparatus of claim 12, wherein the simulated signal is passed through a high-pass filter to obtain a high-pass signal.

14. The apparatus of claim 13, wherein the output signal of the sensor is passed through a low-pass filter to create a low-pass signal.

15. The apparatus of claim 14, wherein the low-pass signal and the high-pass signal are combined to create the feedback signal.

16. The apparatus of claim 14, wherein the low-pass filter and the high-pass filter sum to substantially one.

17. A method of controlling a system for applying a load to a material, comprising:

applying a final control signal to an actuator which causes the actuator to create the load which can be applied to the material;

causing a sensor to measures an output of the system while the load is being applied to the material;

reading an output signal from the sensor;

processing the final control signal to obtain a simulated signal that has one or more of substantially reduced resonances and substantially reduced phase delay compared to the output signal; and passing the simulated signal through a filter mechanism to obtain a high-pass signal.

18. The method of claim 17, further including passing the output signal of the sensor through the filter mechanism to create a low-pass signal.

19. The method of claim 18, wherein the filter mechanism includes a low-pass filter and a high-pass filter which sum to substantially one.

20. The method of claim 18, further including combining the low-pass signal and the high-pass signal to create a feedback signal.

21. The method of claim 20, further including obtaining a first or higher order derivative of the feedback signal.

22. The method of claim 21, further including inputting to the system a reference signal having a predetermined waveform.

23. The method of claim 22, further including differentially combining the reference signal with the feedback signal to obtain an initial control signal.

24. The method of claim 23, further including differentially combining the initial control signal with the derivative of the feedback signal to obtain the final control signal.

25. The method of claim 17, wherein the sensor measures a characteristic of the material.

\* \* \* \* \*